(12) United States Patent
Dakin et al.

(10) Patent No.: US 8,908,160 B2
(45) Date of Patent: Dec. 9, 2014

(54) OPTICAL AIR DATA SYSTEM SUITE OF SENSORS

(75) Inventors: Elizabeth A. Dakin, Great Falls, VA (US); Priyavadan Mamidipudi, Bristow, VA (US); Philip L. Rogers, Hume, VA (US); Daniel C. Dakin, Great Falls, VA (US)

(73) Assignee: Optical Air Data Systems, LLC, Manassas, VA (US)

( * ) Notice: Subject to any disclaimer, the term of this patent is extended or adjusted under 35 U.S.C. 154(b) by 87 days.

(21) Appl. No.: 13/478,025

(22) Filed: May 22, 2012

(65) Prior Publication Data

US 2013/0162974 A1   Jun. 27, 2013

Related U.S. Application Data

(60) Provisional application No. 61/580,039, filed on Dec. 23, 2011, provisional application No. 61/578,866, filed on Dec. 23, 2011, provisional application No. 61/604,925, filed on Feb. 29, 2012.

(51) Int. Cl.

| G01N 21/53 | (2006.01) |
|---|---|
| G01P 13/02 | (2006.01) |
| G01S 17/58 | (2006.01) |
| G01N 21/64 | (2006.01) |
| G01P 5/26 | (2006.01) |
| G01S 7/481 | (2006.01) |
| G01S 17/95 | (2006.01) |

(52) U.S. Cl.
CPC ............... *G01N 21/53* (2013.01); *G01S 7/4812* (2013.01); *G01P 13/025* (2013.01); *G01S 17/58* (2013.01); *G01S 7/4818* (2013.01); *G01N 21/6408* (2013.01); *G01S 17/95* (2013.01); *G01P 5/26* (2013.01)
USPC .......................................... 356/28; 356/28.5

(58) Field of Classification Search
CPC ......... G01N 21/53; G01C 3/08; G01P 13/025
USPC ............. 356/3.01–3.15, 4.01–4.1, 5.01–5.15, 356/6–22, 28, 28.5
See application file for complete search history.

(56) References Cited

U.S. PATENT DOCUMENTS

| 4,483,614 A | 11/1984 | Rogers |
|---|---|---|
| 4,506,979 A | 3/1985 | Rogers |

(Continued)

FOREIGN PATENT DOCUMENTS

WO   WO 2009/134221 A1   11/2009

OTHER PUBLICATIONS

Bowles, R. L., "Windshear Detection and Avoidance: Airborne Systems Survey," Proceedings of the 29th Conference on Decision and Control, Institute of Electrical and Electronics Engineers, United States, 1990; pp. 708-736.

(Continued)

*Primary Examiner* — Luke Ratcliffe
(74) *Attorney, Agent, or Firm* — Caeser, Rivise, Bernstein, Cohen & Pokotilow, Ltd.

(57) ABSTRACT

Systems and methods for laser based measurement of air parameters for use, e.g., on aircraft are disclosed. An example system includes a coherent source of radiation, a modulator, a transceiver, an optical mixer, and a measuring system. The coherent source produces a coherent radiation beam, and the modulator is configured to modulate the coherent radiation beam. The transceiver is configured to transmit the modulated radiation beam to, and receive a scattered radiation signal from a target region. The optical mixer is configured to determine a difference between the scattered radiation signal and the reference radiation beam. The measuring system is configured to determine at least one of velocity, air density, pressure, temperature, barometric altitude, angle of attack, angle of side slip, icing and turbulence based on the difference between the scattered radiation signal and the reference radiation beam.

8 Claims, 11 Drawing Sheets

(56) References Cited

U.S. PATENT DOCUMENTS

| | | | |
|---|---|---|---|
| 4,572,667 | A | 2/1986 | Rogers |
| 4,718,121 | A | 1/1988 | Epworth |
| 4,875,770 | A | 10/1989 | Rogers et al. |
| 5,272,513 | A * | 12/1993 | Vahala et al. ............ 356/28.5 |
| 5,307,197 | A | 4/1994 | Tanabe et al. |
| 6,751,532 | B2 | 6/2004 | Inokuchi |
| 6,856,396 | B2 | 2/2005 | McGuire |
| 6,871,816 | B2 | 3/2005 | Nugent et al. |
| 7,463,341 | B2 | 12/2008 | Halldorsson et al. |
| 7,523,657 | B2 | 4/2009 | Bommier et al. |
| 7,777,866 | B1 | 8/2010 | Kyrazis |
| 2011/0037970 | A1 | 2/2011 | Rogers et al. |
| 2011/0043785 | A1 | 2/2011 | Cates et al. |
| 2011/0188029 | A1 | 8/2011 | Schmitt et al. |
| 2011/0292371 | A1 | 12/2011 | Chang |
| 2012/0206712 | A1 | 8/2012 | Chang et al. |

OTHER PUBLICATIONS

Haverdings, H., et al., "Quick Access Recorder Data Analysis Software for Windshear and Turbulence Studies," Journal of Aircraft, vol. 47, No. 4, American Institute of Aeronautics ans Astronautics, United States, Jul.-Aug. 2010; pp. 1443-1446.

Inokuchi, H. et al., "Development of an Onboard Doppler Lidar for Flight Safety," Journal of Aircraft, vol. 46, No. 4, American Institute of Aeronautics and Astronautics, United States, Jul.-Aug. 2009; pp. 1411-1415.

Jenaro Rabadan, G., et al., "Airborne Lidar for Automatic Feedforward Control of Turbulent In-Flight Phenomena," Journal of Aircraft, vol. 47, No. 2, American Institute of Aeronautics and Astronautics, United States, Mar.-Apr. 2010; pp. 392-403.

U.S. Appl. No. 13/475,536, Dakin et al., "High Power Laser Doppler Velocimeter With Multiple Amplification Stages," filed May 18, 2012.

U.S. Appl. No. 13/477,454, Dakin et al., "LDV System for Measuring Wind at High Altitude," May 22, 2012.

U.S. Appl. No. 13/628,704, Dakin et al., "Laser Doppler Velocimeter Optical Electrical Integrated Circuit," filed Sep. 27, 2012.

* cited by examiner

OPTICAL AIR DATA SYSTEM SUITE OF SENSORS

CROSS REFERENCE TO RELATED APPLICATIONS

This application claims benefit under 35 U.S.C. §119(e) to U.S. Provisional Patent Application Nos. 61/580,039 and 61/579,866, both filed on Dec. 23, 2011, and U.S. Provisional Patent Application No. 61/604,925 filed on Feb. 29, 2012, which are each incorporated by reference herein in their entirety.

This application is related to non-provisional application Ser. No. 13/477,454 (Title: "LDV System for Measuring Wind at High Altitude") also filed on May 22, 2012, which is also incorporated herein by reference in its entirety.

BACKGROUND

1. Field

This disclosure relates to the field of measurement of air and wind parameters.

2. Background Art

Conventionally, relative air speed is measured between a moving object, such as any airborne vehicle, e.g., an aircraft or helicopter, and the free airstream through which the airborne vehicle is flying using a mechanical instrument that compares the kinetic pressure, exerted by the moving airstream onto a first area facing the airstream with respect to the static pressure exerted on a second area generally perpendicular to the first area. Typically, such a conventional system employs pitot tubes, pneumatic tubing, and pressure transducers, which are exposed to the external environment and subject to not only degraded performance caused by calibration changes, but also catastrophic failures as a result of accidental breakage. Furthermore, this conventional type of air speed measurement device physically protrudes into the airflow, with a resultant drag penalty.

Also, conventionally, changes in altitude were measured using mechanical instruments sensitive to changes in pressure of the earth's atmosphere from one elevation to another. Accordingly, it is conventional to provide an aircraft with one or more static pressure ports so that the external air pressure is exerted upon a pressure measuring diaphragm contained within the aircraft.

However, significant inaccuracies may result from disturbances by the airflow in the region of the pressure port caused by icing, by air currents and turbulence, and by air compression effects or from changes in the orientation of the port relative to the airflow caused by changes in the attitude (i.e., the orientation relative to the ground) of the aircraft.

Furthermore, conventional approaches do not provide reliable systems and methods for making air data measurements at a sample location at a sufficient distance from the aircraft or any physical attachments thereto such that the measurement will not be subject to systemic errors of a sort that cannot always be fully compensated for such as those caused by air compression effects and airflow disturbances.

BRIEF SUMMARY

Therefore, what is needed are systems and methods for laser based measurement of air parameters for use on aircraft.

An example system including a coherent source of radiation, a modulator, a transceiver, an optical mixer, and a measuring system is disclosed. The coherent source produces a coherent radiation beam, and the modulator is configured to modulate the coherent radiation beam. The transceiver is configured to transmit the modulated radiation beam to, and receive a scattered radiation signal from a target region. The optical mixer is configured to determine a difference between the scattered radiation signal and the reference radiation beam. The measuring system is configured to determine at least one of velocity, air density, pressure, temperature, barometric altitude, angle of attack, angle of side slip, icing, and turbulence, based on the difference between the scattered radiation signal and the reference radiation beam.

In a further embodiment, a method for laser based determination of air parameters is disclosed. This method includes generating a coherent radiation beam and modulating the coherent radiation beam to produce a modulated radiation beam. The method further includes transmitting the modulated radiation beam to a target region and receiving a scattered radiation signal from the target region. Further the method includes receiving a reference radiation beam from the coherent source, and determining a difference between the scattered radiation signal and the reference radiation beam. Lastly the method includes determining at least one of velocity, air density, pressure, temperature, barometric altitude, angle of attack, angle of side slip, icing, and turbulence, based on the difference between the scattered radiation signal and the reference radiation beam.

An embodiment of the present invention provides a method of using a light detection and ranging (LIDAR) system. A beam of radiation is transmitted to target areas at least one of above, below, and in front of an airborne vehicle, the target areas including at least one of one or more particles or one or more objects. Scattered radiation is received from the target areas. Respective characteristics, for example, a wind profile, of the scattered radiation are determined. At least one of an air turbulence factor or a distance to the one or more objects is determined from the respective characteristics. In one example, the airborne vehicle is controlled based on the air turbulence factor, such that turbulence experienced by the airborne vehicle is minimized.

In further embodiments, true airspeed can be determined by correcting the measured velocity for effects due to turbulence. The disclosed embodiments are more accurate than traditional systems (e.g., pitot tubes) at low velocities.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 7:
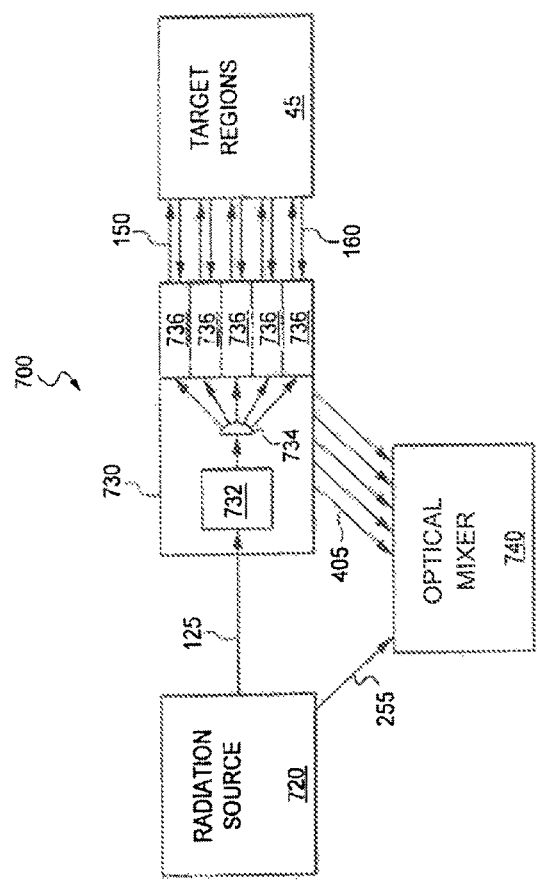
Figure 8:
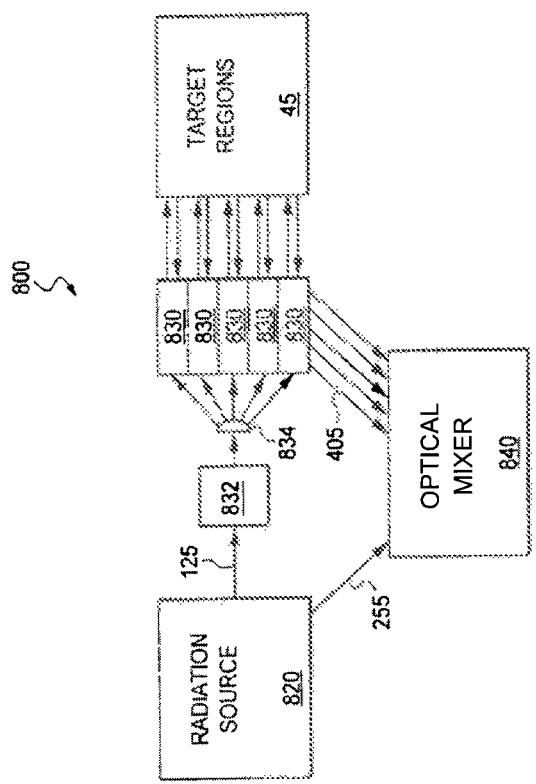
Figure 9:
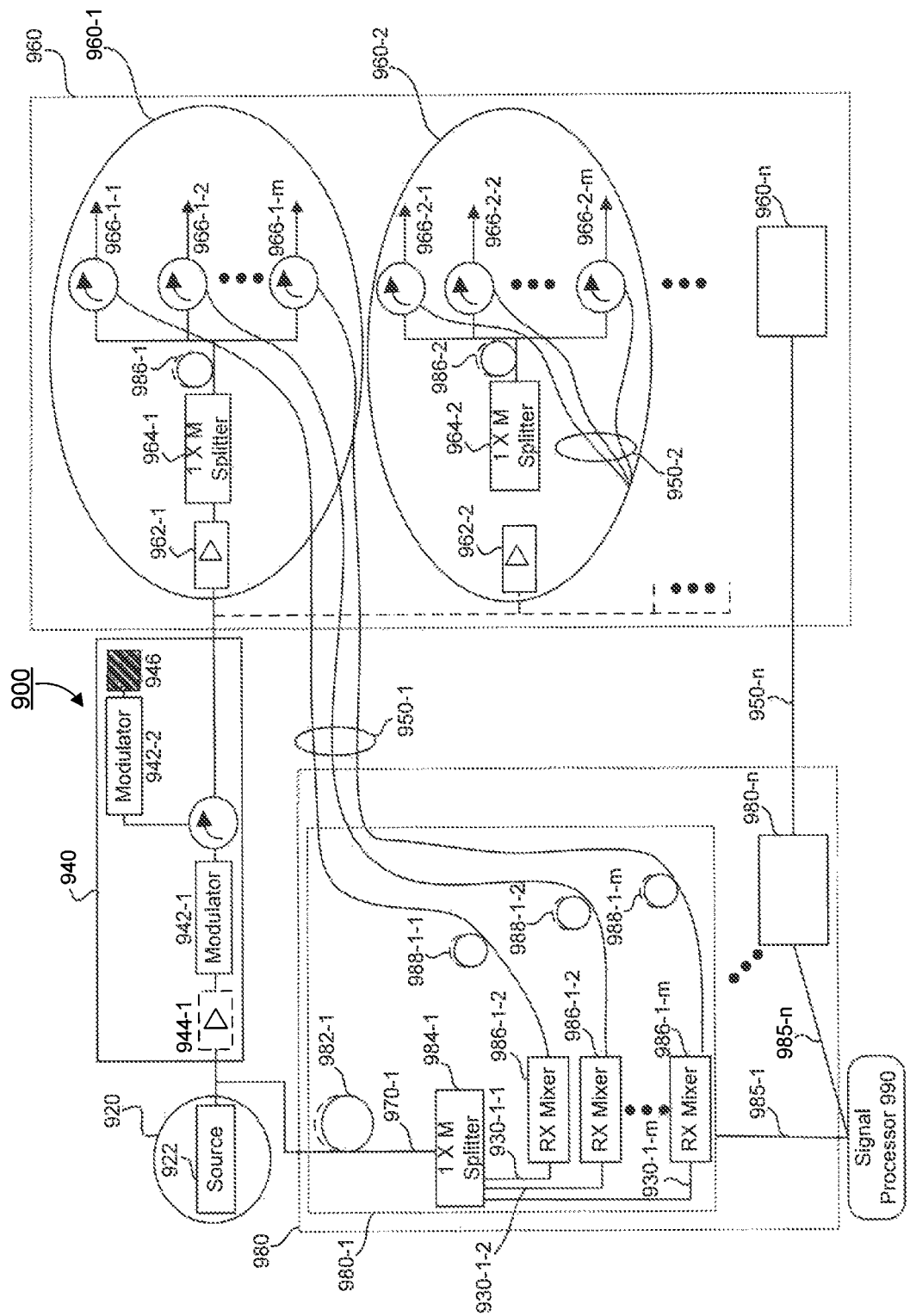

FIGS. 7, 8, and 9, illustrate various embodiments of laser Doppler velocimeters with multiple transceivers.

Figure 10:
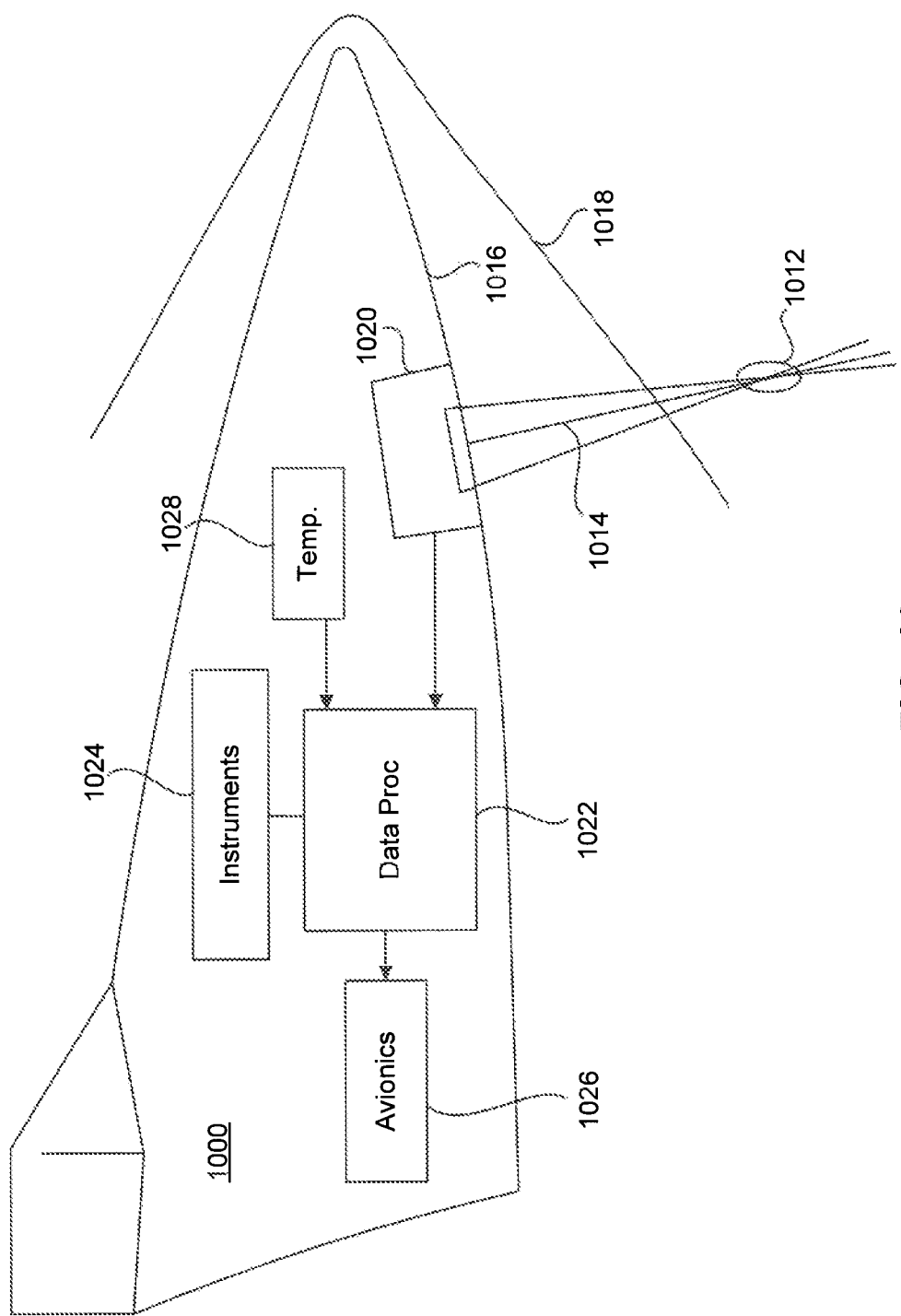

FIG. 10 illustrates an aircraft, according to an embodiment of the present invention.

Figure 11:
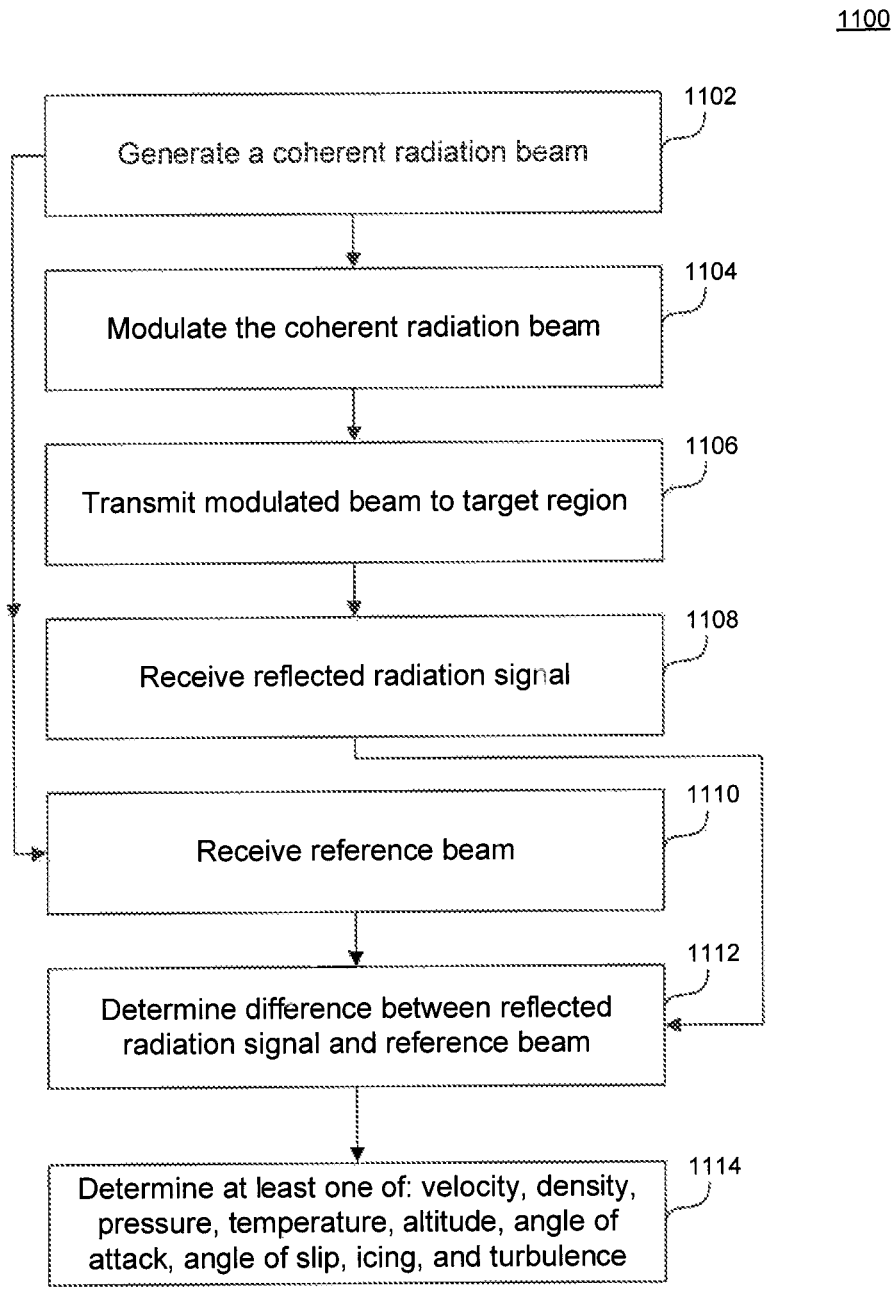

FIG. 11 is a flow chart illustrating a method for laser based determination of air parameters.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to affect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
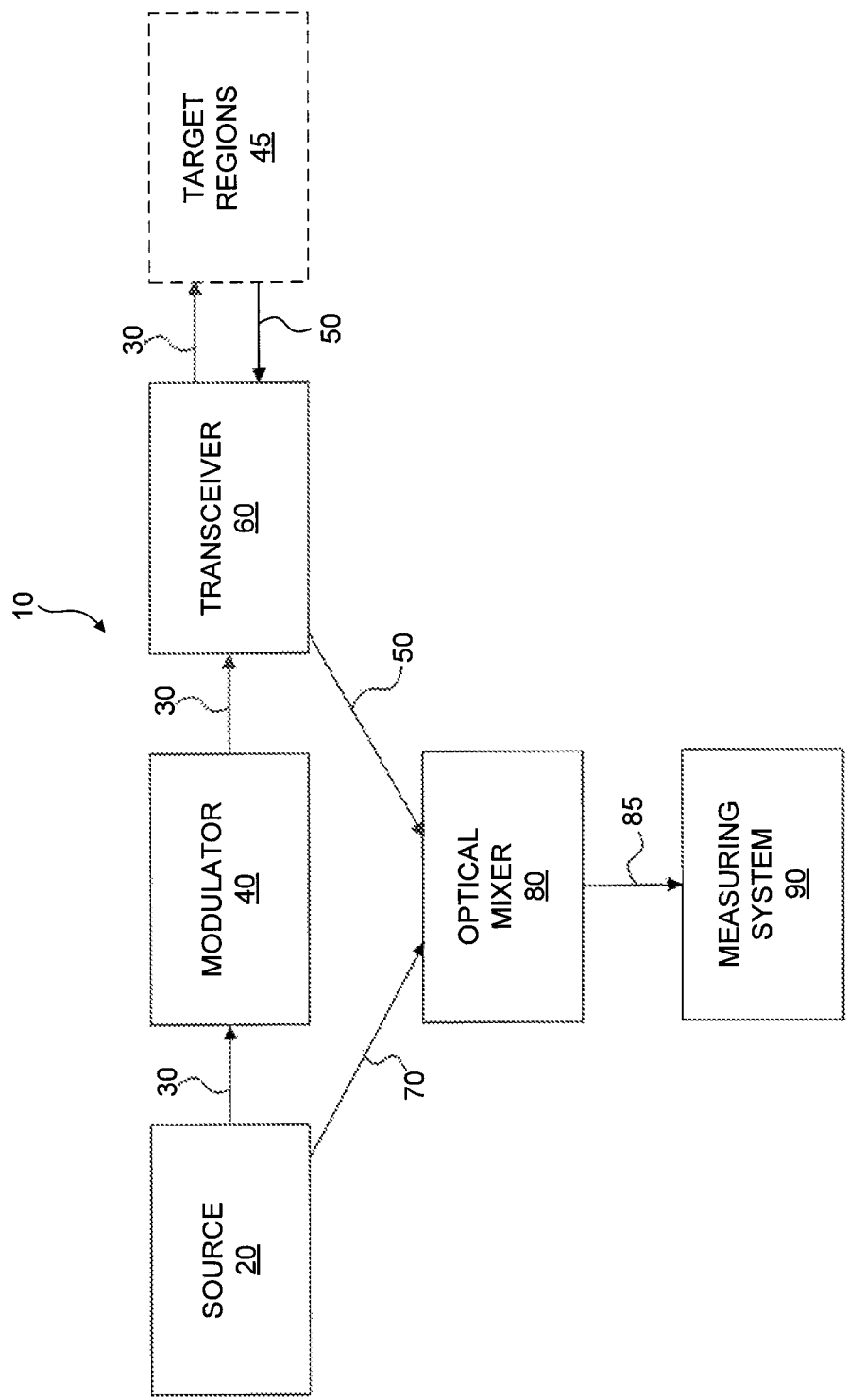
FIG. 1 illustrates a laser Doppler velocimeter.

An example of an air speed LDV 10 is illustrated in FIG. 1 and as disclosed in U.S. Pat. No. 5,272,513, the disclosure of which is incorporated herein by reference in its entirety. The determination of air data parameters is also disclosed in U.S. Pat. Nos. 4,483,614; 4,506,979; 4,572,667, and 4,875,770, which are each incorporated by reference herein in their entirety.

Various embodiments described herein can also be used in conjunction with the systems and methods disclosed in U.S. Provisional Patent Application No. 61/604,925. In an embodiment, a LDV system is considered for use on an airborne vehicle to measure wind profile substantially close to the airborne vehicle. In an example, the LDV system measures airspeeds at distances less than 2000 feet directly above and below the airborne vehicle. In another example, the LDV system measures airspeeds at distances less than 2000 feet directly in front and behind the airborne vehicle. In another example, the LDV system receives scattered radiation from distances a few miles in front of the airborne vehicle.

The LDV 10 includes a source 20 of coherent light which may, if desired, be polarized. The source 20 projects a first coherent beam of light 30 into a modulator 40. The modulator 40 expands and collimates the beam 30 after which beam 30 enters a transceiver 60. The transceiver 60 projects the beam 30 in nearly collimated form into the target region 45.

The collimated beam strikes airborne scatterers (or air molecules) in the target region 45, resulting in a back-reflected or scattered beam 50. A portion of the scattered beam 50 is collected by the same transceiver 60 which transmitted the beam 30, or to an adjacent receiver (not shown). The case where the same transceiver transmits and receives the light is known as a monostatic configuration, while the case of separate transmitters and receivers is known as a bistatic configuration. Monostatic configurations can only receive scattered light. Bistatic configurations can be arranged to receive light that is substantially scattered or at any other angle relative to the transmitted beam 30.

The light 50 collected by transceiver 60 is then combined with a separate reference beam of light 70 in an optical mixer 80. An ideal optical mixer combines the two beams in such a way that they have the same polarization and occupy the same space, and directs the result onto a photo detector with a bandwidth sufficient to detect the measured Doppler frequency shift. The photo detector produces an electrical current 85 which includes a component whose frequency is the mathematical difference between the frequency of the reference beam 70 and the scattered beam 50. The electrical current 85 is then analyzed by a signal processor 90 (e.g. electrical spectrum analyzer or a frequency counter) to determine the frequency difference and calculate the relative velocity component along the axis of the transceiver 60 between the LDV 10 and the target region 45.

Ambiguities regarding whether the measured relative frequency is either positive or negative can be resolved by using the "in-phase and quadrature" detection method, as is known in the art. Another approach to resolving these ambiguities is to apply a stable, constant frequency shift either to the transmitted beam 30 or to the reference beam 70 (e.g. by using an acousto-optic cell). This creates an alternating current component in the electrical signal 85 with a frequency that is the sum of the constant frequency shift and the Doppler frequency shift, removing the directional ambiguity. An LDV wherein the frequency of the transmitted beam 30 and the frequency of the reference beam 70 are identical is said to use homodyne detection. Heterodyne detection is used when the frequencies of the transmitted beam 30 and reference beam 70 are different.

The reference beam 70 is selected to have a well-defined and stable optical frequency that bears a constant phase relationship with the transmitted beam 30. This is known as coherence. The requirement for coherence is easily achieved by using a laser as the source 20 and tapping the source 20 to create the reference beam 70 by means of an optical splitter (not shown).

Source 20 can be either a $CO_2$, Nd:YAG, or Argon Ion laser (preferably lasing in the fundamental transverse mode and in a single longitudinal mode). However, air-speed targets (aerosols and/or molecules) generate very weak return signals compared to solid objects. Thus air-speed LDV's incorporating these laser sources that work over a range of thousands or even tens of meters require large amounts of laser power and are thus too large, bulky, heavy, fragile and possibly dangerous to be used in many desirable applications like air-speed determination for helicopters.

However, source 20 can also be a lightweight, low-cost, highly efficient, rare-earth-doped glass fiber (referred to hereafter as a fiber laser). Fiber lasers have several enormous advantages over other laser sources. Fiber lasers can be efficiently pumped by laser diodes whose emission wavelengths have been optimized for excitation of the rare-earth dopant. This makes the fiber lasers very energy efficient and compact, eliminating the need for cooling systems, flash lamps, and high current electrical sources. Moreover the glass fiber serves as a flexible waveguide for the light, eliminating the need for bulky optical components like mirrors and lenses that require rigid mechanical mounts in straight lines with stringent alignment tolerances. Fiber lasers are also more adaptable than solid-state lasers: the pulse repetition frequency ("PRF") and pulse width in fiber lasers may be changed "on the fly," while the PRF and pulse width in solid-state lasers are bound to narrow ranges or are even fixed. Source 20 can also be comprised of a laser diode coupled to an optical fiber.

Despite advances in conventional LDV's, improvements are still necessary. Sometimes it is desirable to locate the source laser 20 at a different, more accessible location than the transceiver 60. For example, in a wind turbine generator ("WTG") application the telescope can be located on the turbine, while its source laser and control electronics are best located in the nacelle or at the base of the tower that supports the WTG for ease of maintenance. In sailing applications the source is preferably located within the hull of the ship where it is protected from exposure to the elements.

These remote configurations can be made conveniently by using optical fiber to connect the source laser 20 and the transceiver 60. Problems have occurred, however, in that the large optical power required for air speed measurements becomes limited by a non-linear effect that occurs in fiber optics known as stimulated Brillouin scattering ("SBS"). In fact, the longer a fiber optic is, the lower this limit becomes. The SBS power limit depends on other factors known to those skilled in the art, but it is a fundamental physical property of light traveling through transparent media and cannot be ignored.

Additional exemplary systems are taught in co-owned U.S. application Ser. No. 12/988,248 and PCT Appl. No. WO 2009/134221, which are both incorporated by reference herein in their entireties.

Embodiments of the present invention provide a velocimetry system for an LDV with no moving parts and which is lightweight enough to be used for many different applications which were, up to this point, not practical for LDVs. The disclosed LDV includes an active lasing medium, such as e.g., an erbium-doped glass fiber amplifier for generating and amplifying a beam of coherent optical energy and an optical system coupled to the beam for directing the beam a predetermined distance to a scatterer of radiant energy. The scattered beam is mixed with a reference portion of the beam for determining the velocity of the scatterer.

In using this device to measure wind velocity in the transceiver focal volume, the velocity component that is measured is that component along the axis of the transceiver. Therefore, for measurement of the "n" components of velocity, n independent measurements must be made along n non-collinear axes (where n is an integer). To accomplish this task n duplicate transceivers are disclosed, each carrying either a continuous wave ("CW") beam or are simultaneously pulsed with a common seed laser source. Simultaneous pulsing and transmission through the n transceivers has the advantage that the velocity measurements each arise from the same moment in time, instead of from sequential moments in time. Thus, the resulting velocity determinations are more accurate as a result of simultaneous pulsing and transmission instead of sequential transmission.

By using optical fiber for both generation of the laser energy as well as wave guiding of the energy, the present disclosure provides a single, mechanically flexible conduit for light. This configuration allows the system to be more robust to vibration and temperature variation than a corresponding system comprising free space optical components. The only point at which light leaves the optical fiber system is for projection from the respective transceivers. Each of the optical fibers that transmits light is also the same fiber used to receive scattered light and thus the aerosol-scattered return beam is automatically aligned with the respective transceiver-fiber optic collection systems.

The use of fiber lasers such as e.g., erbium-doped optical fiber also has advantages in terms of the overall energy efficiency of the system. Because diode lasers are now available at the optimal pump wavelength of erbium doped glass, the erbium wave guide can be efficiently pumped by launching pump radiation down this wave guide. Thus, the system has greatly reduced cooling requirements and can operate off of a low voltage battery supply.

The disclosed velocimeter system is also eye-safe, lightweight, and easily scaled to high energy per pulse or CW operation. As described above, the velocimeter has "n" lines of sight. Thus, in order to determine an object's velocity or the wind velocity in one or more target regions, n transceivers are used, each simultaneously projecting a beam of light along a different axis. To determine three-dimensional velocity, as with wind velocity, three transceivers are used. To determine two- or one-dimensional velocity, e.g., for a car or boat moving on a plane or in a line, fewer transceivers may be used. The laser beams projected from the n transceivers are each pumped simultaneously and arise from a single laser source. The source may be co-located with the n transceivers, or may be located remotely with respect to the n transceivers. If the laser source is remotely located, fiber optic cables are used to carry the generated light beams to each transceiver. As described below in greater detail, a seed laser from the source is amplified and, if desired, pulsed and frequency offset, and then split into n source beams. The n source beams are each delivered to an amplifier assembly that is located within the n transceiver modules, where each of the n transceiver modules also includes an optical system such as a telescope. Amplification of the n source beams occurs at the transceiver modules, just before the n beams are transmitted through the optical system to one or more target regions. Thus, when the n source beams are conveyed through connecting fibers from the laser source to each of the n transceivers, the power of each of the source beams is low enough so as not to introduce non-linear behaviors from the optical fibers. Instead, power amplification occurs in the transceiver module, just before transmission from the optical system. Consequently, fiber non-linear effects are not introduced into the system.

The placement of the power amplifier within the transceiver modules just before laser beam projection through a lens reduces the effect of nonlinear fiber behavior that is normally observed when there is a greater propagation distance between the power amplifier and the lens. In this way, the disclosed velocimeter is able to use a single seed laser and amplifier assembly that is remote from the power amplifier. The seed laser generates a beam that may be amplified, pulsed, and frequency shifted before the beam is split, if necessary, and directed to the remote power amplifiers. Power amplification only occurs just before transmission of the source beam through the lenses. Thus, as long as the amplified result is still within the linear operating region of the fiber to the remote amplifier, the disclosed velocimeter avoids the problems associated with non-linear fiber operation.

By using the disclosed velocimeter, object or wind velocities may be measured with a high degree of accuracy. Because the source laser is split into n beams, the measurements taken along all of the n axes are simultaneous. Additionally, splitting the source beam into n beams does not necessarily require that the source laser transmit a laser with n times the necessary transmit power, because each of the n beams are subsequently power amplified before transmission. The n beams may each be directed towards the same target region or may be directed to multiple target regions. A single beam may be used to simultaneously measure velocities at multiple points or span along a single axis. Additionally, the disclosed velocimeter has no moving parts, and is thus of reduced size and improved durability. As explained below, the disclosed velocimeter may be used with a platform motion sensing device such as e.g., an inertial measurement unit ("IMU") or global positioning satellite ("GPS") unit so that the motion of the velocimeter platform may be compensated during calculation of the measured velocities. Thus, because of the lightweight and non-bulky nature of the velocimeter, and because of the velocimeter's ability to compensate for platform motion, the disclosed LDV may be mounted on any moving platform (e.g., a helicopter, a boat, etc.) and still obtain highly accurate readings.

Figure 2:
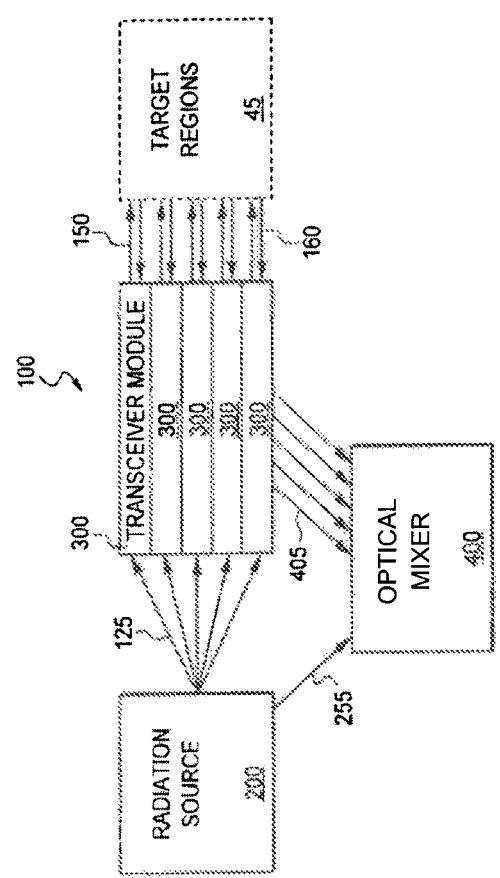
FIG. 2 illustrates an embodiment of a laser Doppler velocimeter with multiple transceivers.

FIG. 2 is a block diagram illustrating an n-axis laser Doppler velocimeter system 100. The system 100 includes a radiation source module 200, n transceiver modules 300, and an optical mixer 400. Each of the modules are described in detail below. The radiation source module 200 generates n source beams 125 to the n transceiver modules 300. The n transceiver modules 300 are for transmitting n beams of light 150 and receiving n scattered or scattered beams of light 160. The transceiver modules 300 may be located in a physically separate location than the radiation source 200 and the optical mixer 400. Alternatively, depending upon the application, all modules may be co-located. The radiation source module 200 also outputs a reference beam 255 to the optical mixer 400. The optical mixer 400 combines the reference beam 255 with each of the scattered/reflected beams 160 received by the n transceiver modules 300 that are passed on to the optical mixer 400 via optical fiber 405. Doppler shifts and hence, velocities, are calculated from the results of the combined signals.

Figure 3:
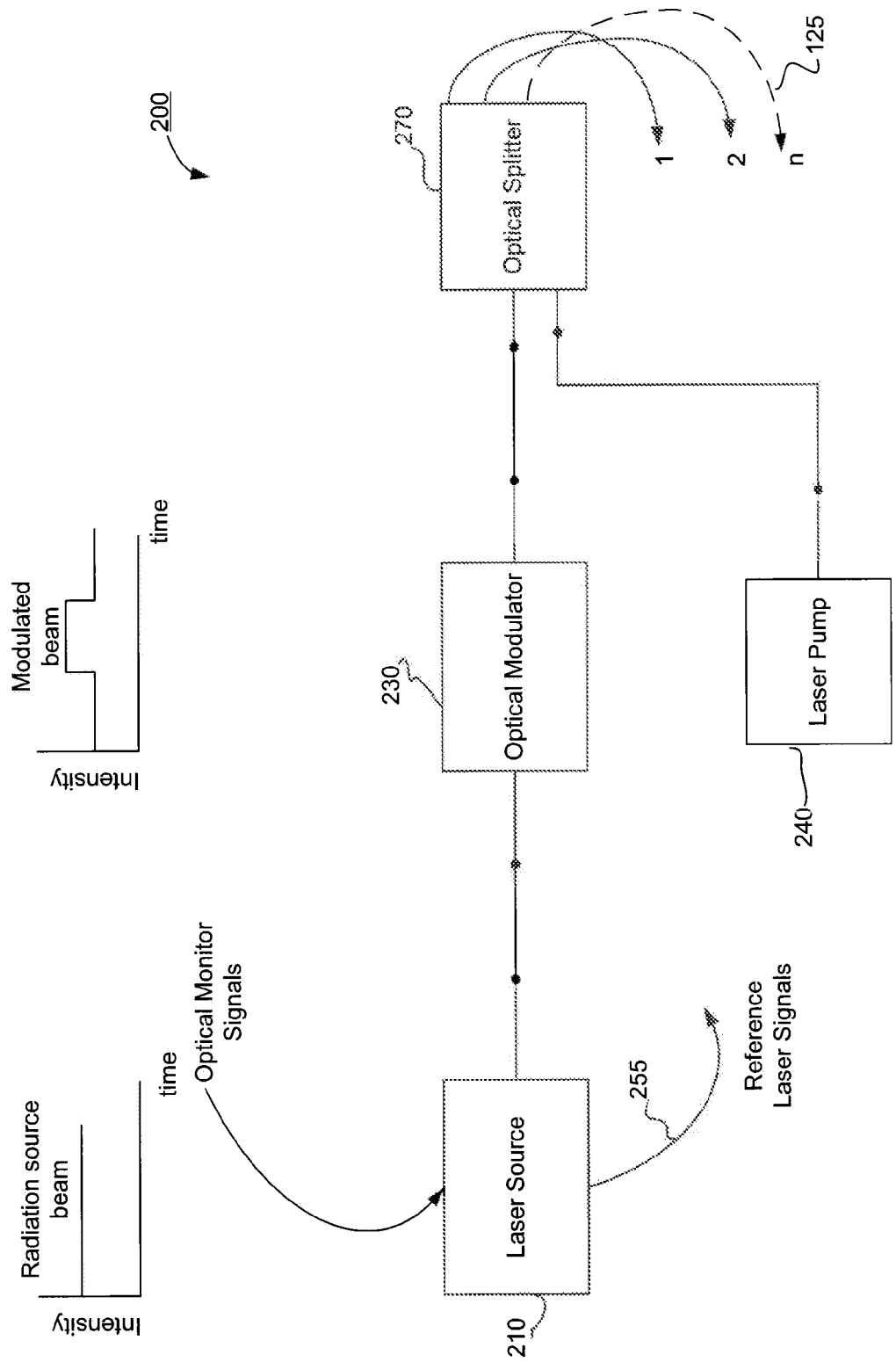
FIG. 3 illustrates an embodiment of a radiation source of the laser Doppler velocimeter.

The radiation source module 200 is illustrated in FIG. 3. The radiation source module 200 includes a laser source 210, an optical amplifier (such as e.g., a fiber optic amplifier, illustrated a 330 in FIG. 4) and an optical splitter 270. The radiation source module 200 may also include an optical modulator 230 to provide a frequency shift (using e.g., an acousto-optic modulator), a polarization shift (using e.g. a Faraday rotator), or both, as well as to induce a temporal pulse shape (i.e. amplitude modulation).

Each of these components of the radiation source module 200 are coupled together and are described in greater detail below.

Figure 4:
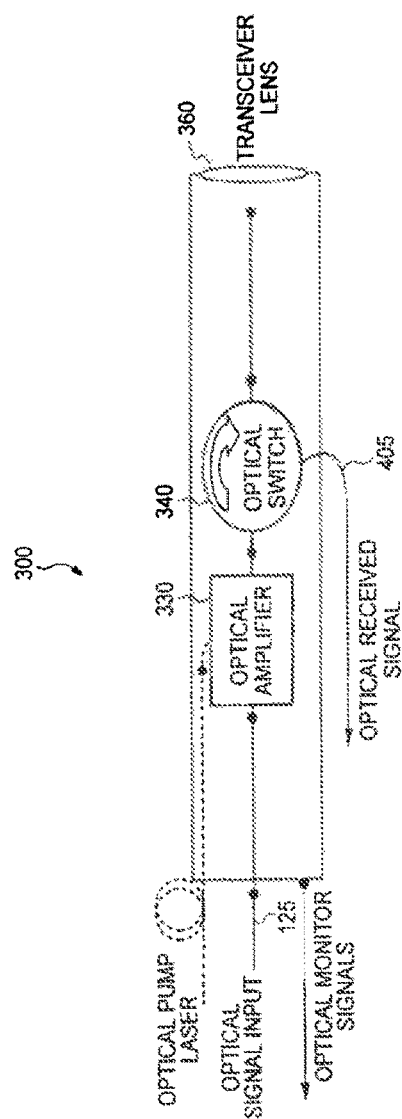
FIG. 4 illustrates an embodiment of a transceiver of the laser Doppler velocimeter.

The laser source 210 and associated drivers and controllers provide the initial laser energy that may be feed into optical amplifier (see FIG. 4, feature 330). When the laser source output is combined with an amplifier, the result is a high power laser output. Typical laser sources 210 are small laser diodes (single-frequency or gain-switched), short-cavity fiber lasers, and miniature solid state lasers such as, for example, nonplanar ring oscillators ("NPROs"), or hybrid silicon lasers. The output from the seed laser source 210 is directed towards the optical modulator 230, that may induce a frequency shift, a polarization shift, or both as well as provide a temporal amplitude modulation. A reference laser signal 255 is also output from the laser source 210.

A frequency shifter (such as an acousto-optic modulator ("AOM")) (as a possible component of the optical modulator 230) and associated RF drivers may provide a radio-frequency ("RF") offset to the laser source output. This offset facilitates the later determination by a signal processor of the direction of any detected motion. The offset is provided by utilizing the acousto-optic effect, i.e., the modification of a refractive index by the oscillating mechanical pressure of a sound wave. In an AOM, the input laser beam is passed through a transparent crystal or glass. A piezoelectric transducer attached to the crystal is used to excite a high-frequency sound wave (with a frequency in the RF domain). The input light experiences Bragg diffraction at the periodic refractive index grating generated by the sound wave. The scattered beam has a slightly modified optical frequency (increased or decreased by the frequency of the sound wave). The frequency of the scattered beam can be controlled via the frequency of the sound wave, while the acoustic power is the control for the optical powers. In this way, a frequency shifter may be used to provide a frequency offset to the laser source output. An AOM may also be used as an optical modulator 230 to modulate laser signals from the source laser 210 in order to obtain pulsed LDV measurements.

Additional modulation of the seed laser output may be provided using an optical modulator 230 (such as e.g., semiconductor optical amplifier ("SOA")). Although the SOA is not necessary for the system 100 to function, SOA-induced pulsing may be used to optimize the extinction ratio in the pulses. The SOA is capable of providing primary as well as secondary modulation of the seed laser source. The SOA may also be used to provide optical amplification to the laser source signal. The laser source 210 can also be modulated electronically.

An optical amplifier (feature 330 in FIG. 4) can be either a semiconductor-based booster optical amplifier ("BOA") or a fiber optic amplifier. The fiber optic amplifier includes a length of fiber doped by a rare earth element such as e.g., erbium (Er), erbuim-ytterbium (Er:Yb), etc. A single mode ("SM") or multimode ("MM") pump diode is used to excite the dopant material within the doped fiber. Optical signals from the SOA may be combined with the pump signals via a wavelength division multiplexer ("WDM") or a tapered fiber bundle ("TFB"). In the optical amplifier 330, the source light is amplified to a level below the power limit dictated by optical damage and nonlinear effects of the fiber. Amplifier spontaneous emission from the optical amplifier 330 is managed via the use of narrowband bulk filters or fiber Bragg grating ("FBG") based filters.

Once filtered, the amplified light is passed through an optical splitter 270. The optical splitter 270 splits the light amongst the different transceiver modules 300. As explained below, the light from the radiation source module 200 is transmitted to optical amplifiers 330 located within each individual transceiver module 300. The use of an optical splitter instead of a switch or multiplexer allows the radiation source module 200 to be designed without any moving parts. In other words, no motors or switches need be used.

Light output from the optical splitter 270 and hence the radiation source module 200 is directed to the n transceiver modules 300 by way of n connecting fibers 125. The connecting fibers 125 allow the radiation source module 200 to be remotely located (if desired) from the n transceiver modules 300. As described above, the lasers carried by the connecting fiber bundle 125 are each at a sufficiently low power to avoid introducing the non-linear effects of the fiber. The fiber bundle 125 consists of multiple fibers of varying core sizes to carry different optical signals between the radiation source module 200 and the n transceiver modules 300. These optical signals include the amplified source laser signal as well as a multimode pump laser signal from a pump laser 240 for the pumping of amplifiers at each of the n transceiver modules 300. Furthermore, optical signals including optical monitor signals from the transceiver modules 300 are carried back to the radiation source module 200. The optical monitor signals can trigger the shutdown of the radiation source module 200 in the event of a malfunction or error at the transceiver modules 300.

One of the n transceiver modules 300 is illustrated in FIG. 4. Each of the transceiver modules 300 includes an optical amplifier 330 (such as a fiber optic amplifier), an optical switch 340 (such as e.g., a fiber optic circulator), and a transceiver lens 360 used to transmit and receive optical signals from the target region 45 (of FIG. 2).

Amplified source laser signals from the radiation source module 200 transmitted via optical fibers 125 to each of the transceiver modules 300 are further amplified within each of the transceiver modules 300 via the optical amplifier 330. The optical amplifier 330 includes a rare earth doped fiber (such as e.g., Er:Yb double clad fiber). Pump light can be introduced into the rare earth doped fiber via a tapered fiber bundle ("TFB") in a co-propagating or counter-propagating manner relative to the seed laser signal from the radiation source module 200. The source laser signal is thus further amplified within the transceiver module 300. The output of the optical amplifier 330 is then directed towards an optical switch 340 via TFBs or WDMs.

The optical switch 340 (such as e.g., a fiber optic circulator) allows a single lens 360 to be used to transmit and receive light, thus allowing the sensor to operate in a monostatic geometry. In the case where multiple lenses are used (at least one for transmitting a light beam and at least one for receiving a scattered light beam, e.g., a bistatic geometry), the optical switch 340 may not be necessary. The optical switch 340 may also be used in conjunction with an amplified spontaneous emission filter. Such a filter might be bulk optic or an FBG based filter. Such a filter may be installed to maintain laser eye safety, as necessary. It is often the case that these filters divert the amplified spontaneous emission ("ASE") to another fiber optic. This diverted laser can be used to monitor the operation of the optical amplifier 330 to adjust the amplifier's power, or as a safety feature in remotely pumped applications. As a safety feature, a measurable drop in the diverted ASE could mean that the fiber cable has been severed and that the pump should be shut down immediately. Alternatively, to reduce ASE in pulsed applications, the pump lasers themselves may be pulsed in synchronization. Pulsing the pump lasers also reduces power consumption, thus facilitating the use of battery operated systems.

Source light that reaches the transceiver lens 360 is projected onto a target object or region 45 (of FIG. 2). Scattered or reflected light is returned to the transceiver module 300. The transceiver lens 360 collects the scattered light back into the fiber. In the case of monostatic operation, the transceiver lens 360 focuses light back into the transmit fiber where the scattered light is separated out from the transmit beam by the optical switch 340. Otherwise, for example, in the case of bistatic operation, the scattered light is focused into a different fiber. The collected scattered light is carried via fiber 405 to the receiving module 400 of FIG. 2.

Figure 5:
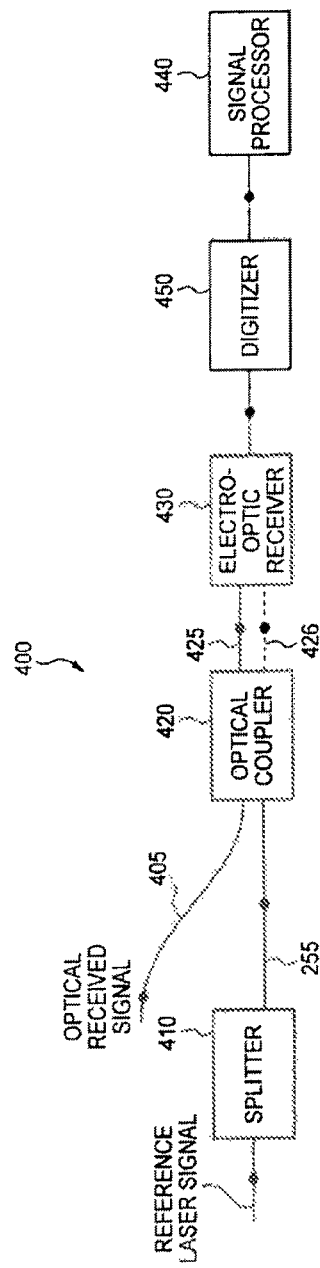
FIG. 5 illustrates an embodiment of a receiver of the laser Doppler velocimeter.

The optical mixer 400 is explained in greater detail with reference to FIG. 5. The optical mixer 400 includes an optical coupler 420 (e.g. a fiber optic coupler) for combining the received signal 405 with the reference laser signal 255 into the same space (e.g., an output optical fiber). This combined signal 425 is then directed onto an electro-optic receiver 430 (e.g. a photodiode) that converts the mixed optical signal into an electrical signal. This signal is then digitized (via a digitizer 450) for convenient signal processing in order to extract the Doppler frequency shift (via a signal processor 440). If n transceiver modules 300 are used then the reference laser signal 255 must be split into n beams by splitter 410 for mixing with n optical mixers 400. If n is large, then an optical amplifier may be required to boost the power of the reference beam 255 before splitting.

An optical coupler such as 420 (e.g., a 3 dB fiber optic coupler) generally produces two output beams 425, 426 of opposite phase. Beam 425 is the combined signal, as explained above. Beam 426 may also be used and applied to a second electro-optic receiver to create a balanced receiver, as described in U.S. Pat. No. 4,718,121, the disclosure of which is incorporated herein by reference. Balanced receivers are preferably used because they use all of the mixed signal, and result in the cancellation of intensity noise in the reference laser beam 255.

Effective optical mixing also requires matching the polarizations of the received signal 405 and the reference laser signal 255. Mitigating the loss of mixing efficiency due to uncontrolled polarization may require a more complicated optical mixing circuit than the one shown in FIG. 5, such as a polarization diversity receiver, described in U.S. Pat. No. 5,307,197, the disclosure of which is incorporated herein by reference.

The signal processor 440 receives the signal from the digitizer 450 and converts the signal into frequency space, calculates line-of-sight speeds from the Doppler shifts along each line-of-sight (i.e., from each of the n transceivers 300), and combines these speeds to determine a single velocity for the target object or region measured. Additionally, the signal processor 440 may use input from a motion sensor (preferably an attitude heading reference system or an IMU and a GPS or ground speed detection device) to determine if the platform upon which the transceivers 300 are mounted is moving. Any platform motion is detected and used to adjust or correct the measured velocity, as described in connection with FIG. 6.

Although not all applications of the disclosed LDV 100 require platform motion compensation, the disclosed LDV 100 (or at least the transceiver module 300 of the LDV 100) is portable and may easily be located on a moving platform such as a boat, ground vehicle or aircraft. As discussed above, the LDV 100 directly measures the relative motion of air scatterers with respect to the transceiver module 300 by detecting the Doppler frequency shift. If the LDV 100 is fixed to the ground, then its measurement is the wind speed and direction. However, an LDV 100 undergoing linear motion measures the relative wind speed and direction. If the linear speed and direction of the moving platform is known, then the wind speed can be extracted from the relative wind measurement. Additionally, the LDV 100 may undergo both linear and rotational motion as encountered on floating platforms. The rotational motion introduces an additional frequency shift since the optical focal volumes are moving rapidly through the air. This frequency shifts yields a speed measurement that is not necessarily useful to (1) meteorologists since it does not represent wind or (2) navigators since it does not represent relative wind. This rotational component must be isolated and compensated for in order to report useful wind data.

Figure 6:
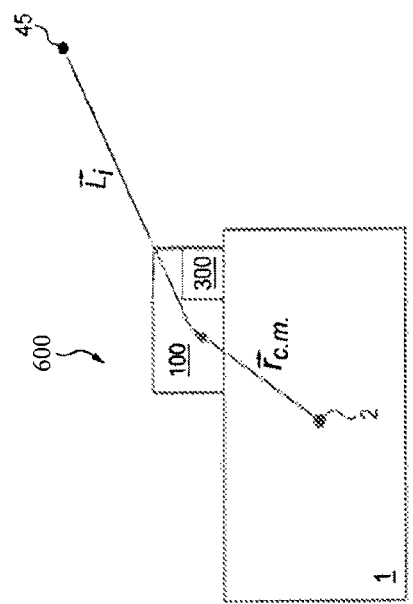
FIG. 6 illustrates a vector diagram of a motion compensation scheme for the laser Doppler velocimeter.

Referring to FIG. 6, a vector diagram of a motion compensation scheme 600 for the disclosed LDV is depicted. Platform motion of platform 1 is composed of linear translations of the platform's center of mass 2 and rotations about the center of mass 2. Mounted on the platform 1 is an LDV 100 with n transceiver modules 300. At least one of the n transceiver modules 300 (e.g., the $i^{th}$ transceiver module 300) is co-located with the LDV 100 on the platform 1. The velocity of the $i^{th}$ focal volume or target region 45 is given by Equation 1, below:

$$\vec{v}_{fi} = \vec{v}_{c.m.} + \vec{\omega} \times \vec{r}_i, \qquad \text{Eq. 1}$$

where $\vec{v}_{c.m.}$ is the linear velocity of the center of mass 2 of the platform 1 (and thus the LDV 100), $\vec{\omega}$ is the angular velocity of the platform 1, and $\vec{r}_i$ is the displacement vector from the center of mass 2 of the platform 1 to the ith focal volume or target region 45. The displacement vector is $\vec{r}_i = \vec{r}_{c.m.} + \vec{L}_i$, where $\vec{r}_{c.m.}$ is a vector from the center of mass 2 of the platform 1 to the transceiver modules 300 and $\vec{L}_i = f\hat{L}_i$ and is a vector from the ith transceiver module 300 to the ith focal volume or target region 45. The magnitude factor f is either the focal length in a focused system or the range in a range-gated system. The Doppler frequency shift created by this velocity is proportional to its component ($\delta_i$) along the laser line of sight $\hat{L}_i$: The $i^{th}$ Doppler frequency shift is equal to $2\delta_i/\lambda$, where $\lambda$ is the laser wavelength and:

$$\delta_i = \vec{v}_{fi} \cdot \hat{L}_i = \vec{v}_{c.m.} \cdot \hat{L}_i + (\vec{\omega} \times \vec{r}_i) \cdot \hat{L}_i. \qquad \text{Eq. 2}$$

The first term of Equation 2 (i.e., $\vec{v}_{c.m.} \cdot \hat{L}_i$) is the desired shift due to the relative linear motion between the target region 45 and the moving platform 1. The second term of Equation 2 (i.e., $(\vec{\omega} \times \vec{r}_i) \cdot \hat{L}$) represents the rotational motion and can be written as $(\vec{r}_{c.m.} \times \hat{L}_i) \cdot \vec{\omega}$ using the rules of cross products with the fact that $(\vec{\omega} \times \vec{L}_i) \cdot \hat{L}_i = 0$. The procedure for motion compensation in a three-dimensional system is to measure the three raw Doppler shifts and the angular velocity with an IMU, then subtract off $(\vec{r}_{c.m.} \times \hat{L}_i) \cdot \vec{\omega}$. This corrected frequency shift is used to compute the three-dimensional relative wind at the $i^{th}$ target region 45.

The angular velocity and attitude (pitch/roll angle) of a moving platform may change rapidly with time. It is important to measure the Doppler shift in a short amount of time so as to allow an assumption that the state motion is frozen (thus allowing the assignment of one value of angular velocity and attitude to each measured Doppler frequency shift). Accordingly, the laser pulse repetition frequency ("PRF") and the number of pulses $N_{acc}$ are chosen so that the total time of data collection (i.e., $N_{acc}$/PRF) is less than 200 milliseconds, for example. The angular velocity is measured before and after the $N_{acc}$ pulses are collected and the average value is used in the compensation calculations for $\vec{\omega}$.

Although LDV 100 has been described in reference to the system and module architectures depicted in FIGS. 2-5, these architectures are exemplary and are not intended to be limiting. For example, FIG. 7 illustrates an additional LDV architecture in the form of LDV 700. As in LDV 100 (of FIG. 2), LDV 700 includes a source module 720, a transceiver module 730 and a optical mixer 740. However, in LDV 700, the source module 720 does not include a splitter. Instead, radiation generated at the source module 720 is conveyed to the transceiver module 730, where the generated radiation is amplified by amplifier 732 and then split via splitter 734 for use by the n transceivers 736 in the transceiver module 730. In LDV 700, only one remote amplifier 732 is used instead of n remote amplifiers.

FIG. 8 illustrates an additional LDV architecture in the form of LDV 800. Here, LDV 800 includes a source module 820, one or more transceiver modules 830 and an optical mixer 840. The source module 820 does not include a splitter. Also, the transceiver modules 830 do not include amplifiers. Instead, an external amplifier 832 and splitter 834 are used. Radiation is generated at the source module 820 is conveyed to the remote amplifier 832 where it is amplified and then split via splitter 834 for delivery to the n transceiver modules 830. As in LDV 700 (of FIG. 7), only one remote amplifier 832 is used in LDV 800.

The disclosed LDV embodiments have been explained in the context of fiber-optic-connected modules in a way that allows the transceiver modules 300, 730, and 830 and optical amplifiers 330, 732, and 832 to be remotely located from the radiation source modules 200, 720, and 820. The transceiver modules 300, 730, and 830 need not include any electronics and can be purely optical modules. Motion compensation, laser sources, and signal processing occurs at the radiation source modules 200, 720, and 820 and optical mixers 400, 740, and 840. Thus, the operation of the transceivers 300, 730, and 830 is significantly improved due to less noise from the radiation source modules 200, 720, and 820 and receiver modules 400, 740, and 840, greater mounting stability and easier maintenance. It is to be understood, however, that the foregoing descriptions of LDVs 100, 700, and 800 are purely exemplary and are not intended to be limiting.

FIG. 9 illustrates a system 900, according to an embodiment of the present invention. In one example, system 900 includes a radiation source 920, a modulator 940, a transceiver 960, an optical mixer 980 and a signal processor 990. These elements may operate similarly to analogous features discussed above. In one example, one or more of modulator 940, transceiver 960, and mixer 980 may include multiple elements, i.e., one or more modulators, one or more transceivers, and one or more mixers, discussed in detail below.

In one example, source 920 is coupled to optical mixers 986-1-1 to **986-*n-m* via respective paths 930-1-1 to 930-*n-m*, transceivers 960-1 to 960-*n* are coupled to optical mixers 980-1 to 980-*n* via respective paths 950-1 to 950-*n*, and optical mixers 980-1 to 980-*n* are coupled to signal processor 990 via respective paths 985-1 to 985-*n***.

In one example, source 920 comprises a coherent radiation source 922, e.g., as a laser. In an example, laser 922 can be a fiber optic laser. In another example, laser 922 can be a rare-earth-doped fiber laser. In another example, laser 922 can be an erbium-doped fiber laser.

In one example, modulator 940 includes one or more modulators 942-1 to 942-n, n being a positive integer. In one example, first modulator 942-1 can operate to introduce a temporal amplitude modulation. In an example, the temporal amplitude modulation induced by modulator 942-1 can be of the form of a pulse. In an example, the temporal amplitude modulation can be of the form of a square wave pulse. In an example, the temporal amplitude modulation can be of the form of a sequence of pulses. In an example, the temporal amplitude modulation can be of the form of a sequence of pulses each with fixed duration of a first time duration separated by a second time duration. In an example, the temporal modulation can be of the form of an arbitrary sequence of pulses of arbitrary shape and duration separated by arbitrary delays. In an example, the temporal amplitude modulation can be of the form of a sequence of square wave pulses.

In an example, modulator 942-1 can be a semiconductor optical amplifier (SOA). In another example, modulator 942-1 can operate to induce a frequency modulation so as to shift the frequency of the source radiation to a higher or lower frequency. In an example, modulator 942-1 can be an acousto-optic modulator (AOM).

In an example, modulator 942-2 can operate to introduce a polarization modulation. In an example, the polarization modulation can be a rotation of the linear polarization of the source radiation. In an example, the polarization modulation can be such as to change a linear polarization of the source radiation into elliptical polarization. In an example, the polarization modulation can change an elliptical polarization of the source radiation into a linear polarization. In an example, modulator 942-2 can be a birefringent crystal. In an example, modulator 942-2 can be coupled to a Faraday rotator 946. In an example, modulator 942-2 can be any device known in the art that operates to introduce a polarization modulation to the source radiation.

In one example, the use of first and second modulators 942-1 and 942-2 in series allows for a pulse amplitude modulation, such as a smaller pulse window (shorter duration and amplitude) within a larger pulse.

In an example, modulator 940 may also contain one or more optical isolators 944-m, where only isolator 944-1 is shown in FIG. 9. Optical isolators can be used to ensure that light propagates only in one direction along an optical fiber just as a diode in an electrical circuit ensures that current only flows in one direction.

In an example, transceiver 960 includes one or more transceiver modules 960-1 to 960-n. Each transceiver module 960-1 can include a splitter 964-1, one or more transceivers 966-1-1 to 966-1-m, m being a positive integer, and an optional delay 968-1. Splitter 964-1 can be a 1×m splitter, splitting a beam received from modulator 940 into m beams, one for each transceiver 966-1 to 966-m. Each of the transceivers 966-1-1 to 966-1-m can comprise similar features and function similarly to transceivers 300 as shown in FIG. 4 and described above.

In one example, delays 968-1 to 968-n are used to adjust the relative phases of the radiation input to transceivers 966-1-1 to 966-n-m to account for differing path lengths between the various transceivers and source 920.

In one example, optical mixer 980 includes one or more mixer modules 980-1 to 980-n. For example, corresponding transceiver modules 960-1 to 960-n are coupled via respective paths 950-1 to 950-n to corresponding optical mixers 980-1 to 980-n. In one example, each mixer module 980-1 to 980-n includes an optional delay 982-n along path 930-n coupled to source 920, a splitter 984-n, one or more mixers 986-1-1 to 986-1-m, and optional delays 988-1-1 to 988-1-n coupled along paths 950-n to respective transceivers 966-1-1 to 966-1-m in respective transceiver modules 960-1 to 960-n.

In one example, delays 982-1 to 982-n can be used to adjust the relative phases of the radiation input to mixers 980-1 to 980-n to account for differing path lengths between the source and mixer modules 980-1 to 980-n

In one example, delays 988-1-1 to 988-n-m can be used to adjust the relative phases of the radiation input to the various mixers 986-1-1 to 986-n-m from the respective transceivers 966-1-1 to 966-n-m to account for differing path lengths between the respective mixers and transceivers.

In one example, splitter 984-1 can split a beam from source 920 into m beams that travel to corresponding mixers 986-1-1 to 986-1-m along respective paths 930-1-1 to 930-1-m. As discussed above, the optical mixers can measure a Doppler shift associated with radiation received by each transceiver 960 or 966 scattered from the target regions relative to that of the source 920. Thus, the function of the beam splitters 984-n is to provide reference signals from the source 920 to each of the mixers 986 that are needed in order to compare with the scattered radiation signal so as to measure a Doppler shift.

In one example, signals from each of the mixers 980-1 to 980-n are received via paths 985-1 to 985-n at signal processor 990. These signals can be the digitized form of the respective Doppler shifts calculated by the various mixers as described above with reference to FIG. 5. In an example, the signal processor 990 can calculate a velocity component associated with each transceiver 960 or 966.

FIG. 10 illustrates an aircraft 1000, according to an embodiment of the present invention. For example, aircraft 1000 can include a data processor 1022 coupled to a measuring system 1020, instruments 1024, avionics 1026, and a temperature sensor 1028. In one example, measuring system 1020 can be a LASER Doppler Velocimeter (LDV) system, for example, one of the various embodiments discussed above, that measures objects in a sample area 1012.

In one example, a sample volume 1012 is defined by the intersection of laser beams 1014 at the focal point of the transmitting optical subsystem. Sample volume 1012 is located at some distance from the nearest surface 1016 of the aircraft 1000, such that the sample volume 1012 is in fact located in a portion of the airstream undisturbed by the aircraft.

In one example, as an example, the aircraft could be a supersonic aircraft with a shock wave 1018. Sample volumes closer to the aircraft than surface 1018 may be turbulent, while volumes farther than surface 1018 (e.g., sample volume 1012) may be undisturbed by the presence of the aircraft.

In this example, the output of the receiving optical subsystem 1020 can be input to data processor 1022. Data processor 1022 can also have as another input, a temperature signal provided by a conventional temperature sensing subsystem 1028. Using these inputs, data processor 1022 can be utilized to determine many different factors regarding sample volume 1012, with respect to the aircraft e.g., at least one of velocity, air density, pressure, temperature, barometric altitude, angle of attack, angle of side slip, icing and turbulence. Although in the embodiment shown a single measuring device 1020 is used to collect data for determining all of these parameters, in other embodiments one or more, or groups, of these parameters may be measured by one or more additional independent devices.

In one example, air density is also determined. This may be determined via measuring device 1020 and data processor 1022. In another example, for an energy source that is interrupted at regular intervals (which is normally preferred), the fluorescent light intensity decays exponentially, and if the intensity is measured at two different times the decay constant can be obtained. From the decay constant, the air density can be determined. For example, this is described in U.S. Pat. No. 4,483,614, incorporated by reference herein in its entirety. The system is configured to determine changes in induced fluorescence to measure optically the density of the air mass. Air density (D) combined with static temperature (T) can be used to determine pressure altitude ($P_s$). For example, this is also described in detail in disclosed in U.S. Pat. No. 4,483,614.

In one example, by appropriate choice of the frequency of the light emitted by the laser, it is possible to cause only one particular molecular species within the atmosphere to fluoresce with sufficient intensity for such fluorescence to affect the output of the detector. The proportion of N2 within the atmosphere is relatively constant, at least at the elevations at which aircraft are normally operated, and therefore the density of N2 within a given sample of atmospheric air will be a reliable indication of the air pressure and barometric altitude in the vicinity of the sample. Thus a reliable measure of the air density can be obtained by determining the decay constant of N2 fluorescence. In a further embodiment, detection of fluorescent light intensity decays can be used to determine the relative humidity of the target region.

An example system (with reference to FIG. 1) includes a coherent source of radiation 20, a modulator 40, a transceiver 60, an optical mixer 80, and a measuring system 90 (also called a signal processor). The coherent source 20 produces a coherent radiation beam 30, and the modulator 40 is configured to modulate the coherent radiation beam 30. The transceiver 60 is configured to transmit the modulated radiation 30 beam to, and receive a reflected radiation signal from a target region 45. The optical mixer 80 is configured to determine a difference between the scattered radiation signal and the reference radiation beam. The measuring system 90 is configured to determine at least one of velocity, air density, pressure, temperature, barometric altitude, angle of attack, angle of side slip, icing and turbulence based on the difference between the scattered radiation signal and the reference radiation beam.

In a further embodiment, the measuring system is further configured to determine a Doppler shift between the scattered radiation signal and the reference radiation beam and to determine a velocity of scatterers in the target region based on the Doppler shift so as to be representative of a motion of an external airstream.

In a further embodiment, the measuring system can be configured to determine a velocity of scatterers for a plurality of target regions in the external airstream, and compare the measured velocities to characterize the presence of turbulence in the external airstream. For example, measurements can be made from region 1012 to sample the airstream that is undisturbed by the presence of the aircraft and compared with results of measurements made within the given surface 1018. In an example, the surface 1018 can represent the shock wave of a supersonic aircraft.

In a further embodiment, the measuring system can be further configured to obtain data characterizing the aircraft's altitude, and to determine at least one of the aircraft's angle of attack and angle of side slip by combining the attitude data with the velocity of scatterers in the target region. Attitude information can be provided by existing instruments on aircraft, e.g., instrument 1024.

In a further embodiment, the modulator can be further configured to periodically interrupt the coherent radiation beam, whereby at least one particular type of representative molecules within air at the target region will be induced to fluoresce and re-emit radiation, the re-emitted fluorescent radiation decaying in intensity following the interruption of the radiation from the laser. In this embodiment the transceiver 60 can be further configured to receive the re-emitted fluorescent radiation, and the measuring system 90 can be further configured to determine a density of air in the target region based on a time-dependent decay of the re-emitted fluorescent radiation. The relative humidity can likewise be determined from the fluorescence decay.

In a further embodiment, a temperature measuring system 1028 for determining the temperature of air in the target region can be provided. In this embodiment, the measuring system can be further configured to determine the pressure of air in the target region based on the air density and temperature. The measuring system can be further configured to determine the barometric altitude based on the pressure.

In a further embodiment, the measuring system can be further configured to determine the relative humidity of air in the target region based on the characteristics of the re-emitted fluorescent radiation, and to determine the presence of icing conditions based on the air density, temperature, pressure, and relative humidity.

FIG. 11 illustrates a flow chart for a method 1100 for laser based determination of air parameters, according to an embodiment. Method 1100 need not be performed in the order shown, or include all the steps to operate as desired.

In step 1102, a coherent radiation beam is generated.

In step 1104, the coherent radiation beam is modulated to produce a modulated radiation beam.

In step 1106, the modulated radiation beam is transmitted towards a target region.

In step 1108, a scattered radiation signal is received from the target region.

In step 1110, a reference radiation beam from the coherent source is compared to the received scattered beam to determine a difference between the scattered radiation signal and the reference radiation beam.

In step 1112, at least one of velocity, air density, pressure, temperature, barometric altitude, angle of attack, angle of side slip, icing and turbulence are determined based on the received scattered beam and other information. For example, determination of these values and parameters can be calculated as discussed above, below, and in the incorporated by reference documents (U.S. Pat. Nos. 5,272,513 and 4,483,614).

In a further embodiment method, a Doppler shift between the scattered radiation signal and the reference radiation beam can be determined and a velocity of scatterers in the target region based on the Doppler shift so as to be representative of a motion of an external airstream can be determined. In a further embodiment, the presence of turbulence in an external airstream can be determined by determining a velocity of scatterers for a plurality of target regions in the external airstream and comparing the measured velocities to determine differences characteristic of turbulence.

In a further embodiment method, at least one of the aircraft's angle of attack and angle of side slip can be determined by obtaining data characterizing the aircraft's attitude (from existing instrumentation) and combining that data with the measured velocity of scatterers in the target region.

In a further embodiment method, the density of air in the target region can be determined by periodically interrupting the coherent radiation beam, whereby at least one particular type of representative molecules within air at the target region will be induced to fluoresce and re-emit radiation. As described above, the air density can be determined from the measured fluorescence decay. Likewise, the air pressure can be determined as discussed above by combining the measured air density with an independent measure of the temperature. In turn, by determining the pressure, the barometric altitude can be determined.

In a further embodiment method, icing conditions can be determined based on the air density, temperature, pressure, and relative humidity. In such an embodiment, the relative humidity can be determined by observing the fluoresce decay of radiation.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of other related applications. The Applicants therefore rescind any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A system comprising:
a source configured to produce a radiation beam;
a modulator configured to modulate the radiation beam to produce a modulated radiation beam, said modulator being further configured to periodically interrupt the radiation beam, whereby at least one particular type of representative molecules within air at the target region will be induced to fluoresce and re-emit radiation, the re-emitted fluorescent radiation decaying in intensity following the interruption of the radiation from the laser;
a transceiver configured to receive the modulated radiation beam via a first optical fiber and to transmit the modulated radiation beam to a target region and to receive a scattered radiation signal from the target region, said transceiver being further configured to receive the re-emitted fluorescent radiation;
an optical mixer coupled to the transceiver via a second optical fiber and coupled to the source via a third optical fiber, the optical mixer configured to:
receive the scattered radiation signal from the transceiver,
receive a reference radiation beam from the coherent source, and
determine a difference between the scattered radiation signal and the reference radiation beam; and
a measuring system configured to determine at least one of velocity, air density, pressure, temperature, barometric altitude, angle of attack, angle of side slip, icing and turbulence based on the difference between the scattered radiation signal and the reference radiation beam, the measuring system being further configured to determine an air density of air in the target region based on a time-dependent decay of the re-emitted fluorescent radiation.

2. The system of claim 1, further comprising:
a temperature measuring system configured to determine the temperature of air in the target region;
wherein the measuring system is further configured to determine the pressure of air in the target region based on the air density and temperature.

3. The system of claim 2, wherein the measuring system is further configured to determine the barometric altitude based on the pressure.

4. The system of claim 3, wherein the measuring system is further configured to:
determine relative humidity of air in the target region based on characteristics of the re-emitted fluorescent radiation; and
determine presence of icing conditions based on the air density, temperature, pressure, and relative humidity.

5. A method comprising:
generating a radiation beam;
modulating the radiation beam to produce a modulated radiation beam;
transmitting the modulated radiation beam to a target region and receiving a scattered radiation signal from the target region;
receiving a reference radiation beam from the source;
determining a difference between the scattered radiation signal the reference radiation beam; and
determining at least one of velocity, air density, pressure, temperature, barometric altitude, angle of attack, angle of side slip, icing and turbulence based on the difference between the scattered radiation signal and the reference radiation beam;
periodically interrupting the radiation beam, whereby at least one particular type of representative molecules within air at the target region will be induced to fluoresce and re-emit radiation, the re-emitted fluorescent radiation decaying in intensity following the interruption of the radiation from the coherent source;
receiving the re-emitted fluorescent radiation; and
determining an air density of air in the target region based on a time-dependent decay of the re-emitted fluorescent radiation.

6. The method of claim 5, further comprising:
   determining the temperature of air in the target region;
   determining the pressure of air in the target region based on the air density and temperature.

7. The method of claim 6, further comprising determining the barometric altitude based on the pressure.

8. The method of claim 5, further comprising:
   determining the relative humidity of air in the target region based on the characteristics of the re-emitted fluorescent radiation; and
   determining the presence of icing conditions based on the air density, temperature, pressure, and relative humidity.

* * * * *